United States Patent
Jiang et al.

(10) Patent No.: US 9,052,474 B2
(45) Date of Patent: Jun. 9, 2015

(54) CLIP DEVICE FOR FACILITATING INSERTION AND REMOVAL OF A PUSH-PULL FIBER OPTIC CONNECTOR

(71) Applicant: Amphenol Fiber Optic Technology (Shenzhen), Shenzhen (CN)

(72) Inventors: Bolin Jiang, Shenzhen (CN); Songsheng Li, Shenzhen (CN); Min Chen, Shenzhen (CN); Linghua Zhu, Shenzhen (CN)

(73) Assignee: Amphenol Fiber Optic Technology (Shenzhen), Shenzhen (CN)

( * ) Notice: Subject to any disclaimer, the term of this patent is extended or adjusted under 35 U.S.C. 154(b) by 42 days.

(21) Appl. No.: 14/096,143

(22) Filed: Dec. 4, 2013

(65) Prior Publication Data
US 2015/0030289 A1    Jan. 29, 2015

(30) Foreign Application Priority Data

Jul. 23, 2013   (TW) .............................. 102213852 U

(51) Int. Cl.
  *G02B 6/38*      (2006.01)
  *A01N 25/10*     (2006.01)
  *G02B 6/44*      (2006.01)

(52) U.S. Cl.
  CPC .............. *G02B 6/3898* (2013.01); *A01N 25/10* (2013.01); *G02B 6/44* (2013.01); *G02B 6/3893* (2013.01)

(58) Field of Classification Search
  CPC ...... G02B 6/3898; G02B 6/44; G02B 6/3894; G02B 6/3821; G02B 6/3831; G02B 6/3885; G02B 6/4465; A01N 25/10
  See application file for complete search history.

(56) References Cited

U.S. PATENT DOCUMENTS

| | | | | |
|---|---|---|---|---|
| 5,548,677 A | * | 8/1996 | Kakii et al. ..................... | 385/92 |
| 6,220,878 B1 | * | 4/2001 | Poplawski et al. .............. | 439/92 |
| 6,497,516 B1 | * | 12/2002 | Toyooka et al. ................ | 385/78 |
| 6,669,376 B2 | * | 12/2003 | Cheng ............................ | 385/76 |
| 2006/0049318 A1 | * | 3/2006 | Newhouse et al. ............. | 248/71 |
| 2007/0160327 A1 | * | 7/2007 | Lewallen et al. ............... | 385/53 |
| 2007/0172172 A1 | * | 7/2007 | Theuerkorn et al. ............ | 385/53 |

* cited by examiner

*Primary Examiner* — Akm Enayet Ullah
(74) *Attorney, Agent, or Firm* — Curatolo Sidoti Co., LPA; Joseph G. Curatolo; Salvatore A. Sidoti

(57) ABSTRACT

A clip device includes a clip detachably holding an outer housing of a fiber optic connector and having a front engaging portion that is detachably sleeved on the outer housing and that abuts against a protrusion member of the outer housing, and a rear abutting portion that abuts against lateral shoulder faces of the outer housing. A gripping handle extends from the rear abutting portion of the clip. A rearward removal force applied to the gripping handle is transmitted to the protrusion member of the outer housing to facilitate removal of the fiber optic connector. A frontward insertion force applied to the gripping handle is transmitted to the lateral shoulder faces of the outer housing to facilitate insertion of the fiber optic connector.

10 Claims, 4 Drawing Sheets

CLIP DEVICE FOR FACILITATING INSERTION AND REMOVAL OF A PUSH-PULL FIBER OPTIC CONNECTOR

CROSS-REFERENCE TO RELATED APPLICATION

This application claims priority to Taiwanese Application No. 102213852, filed on Jul. 23, 2013, the contents of which are hereby incorporated by reference.

BACKGROUND OF THE INVENTION

1. Field of the Invention

The invention relates to a tool for a fiber optic connector, and more particularly to a clip device for facilitating insertion and removal of a push-pull fiber optic connector.

2. Description of the Related Art

It is generally known that, from time to time, fiber optic connectors, such as MPO connectors, maybe removed from another connector or an adapter. For example, an array of fiber optic connectors may need to be removed from an adapter for repair, replacement or use in a different configuration. These fiber optic connectors are often mounted in tight configurations with little space among them to obtain high connector density. Because the fiber optic connectors are very close to one another, it is difficult for a technician to manually hold one fiber optic connector during insertion or removal. Therefore, it is desirable to have a fiber optic connector that is easy to be inserted into and removed from an adaptor, even in high connector density environments.

SUMMARY OF THE INVENTION

Therefore, an object of the present invention is to provide a clip device for a push-pull fiber optic connector that can facilitate insertion and removal of the fiber optic connector.

According to the present invention, there is provided a clip device for facilitating insertion and removal of a fiber optic connector. The fiber optic connector includes an outer housing that permits a front plug end to extend out thereof. The outer housing has a protrusion member proximate to the front plug end, and a shoulder surface distal from the front plug end. The clip device of this invention comprises a clip and a gripping handle. The clip is configured to detachably hold the outer housing of the fiber optic connector. The clip includes a front engaging portion that is configured to be detachably sleeved on the outer housing of the fiber optic connector and abut against the protrusion member of the outer housing of the fiber optic connector, and a rear abutting portion that is configured to abut against the shoulder surface of the outer housing of the fiber optic connector. The gripping handle extends from the rear abutting portion of the clip.

When the clip holds the outer housing of the fiber optic connector, a rearward removal force applied to the gripping handle is transmitted from the front engaging portion of the clip to the protrusion member of the outer housing of the fiber optic connector, thereby facilitating removal of the fiber optic connector.

When the clip holds the outer housing of the fiber optic connector, a frontward insertion force applied to the gripping handle is transmitted from the rear abutting portion of the clip to the shoulder surface of the outer housing of the fiber optic connector, thereby facilitating insertion of the fiber optic connector.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENT

Referring to FIGS. 2 to 5, the preferred embodiment of a clip device 100 for a push-pull fiber optic connector 200 according to the present invention is shown to include a clip 1 and a gripping handle 2. The clip 1 cooperates with the push-pull fiber optic connector 200 to constitute a connector assembly.

Figure 1:
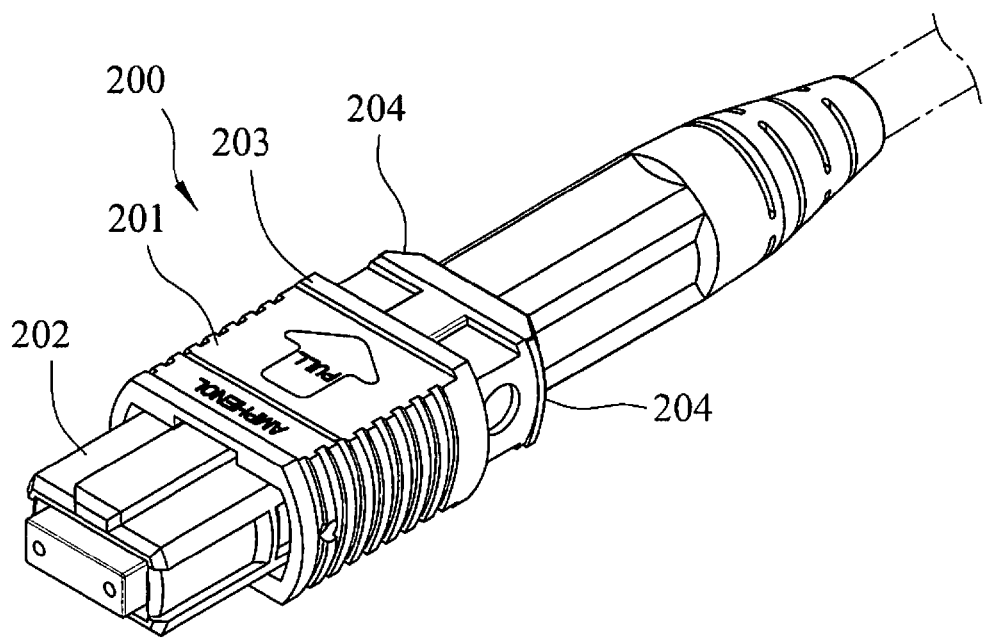
FIG. 1 is a top perspective view showing a push-pull fiber optic connector.
Figure 2:
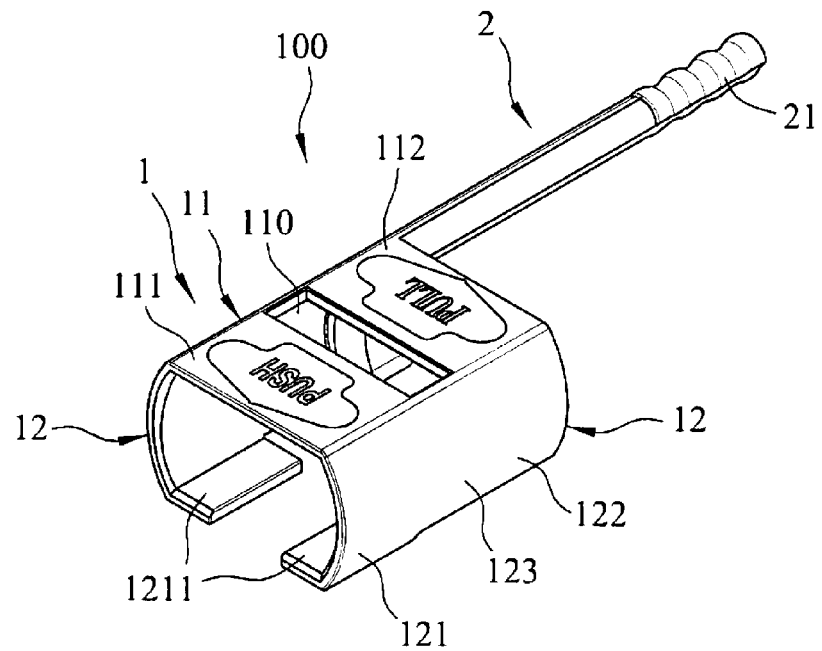
FIG. 2 is a top perspective view showing the preferred embodiment of a clip device for a push-pull fiber optic connector according to the present invention.

As shown in FIG. 1, the fiber optic connector 200, such as a multi-fiber push on (MPO) connector, includes an outer housing 201 that permits a front plug end 202 to extend out thereof. The outer housing 201 has a protrusion member proximate to the front plug end 202, and opposite lateral shoulder faces 204 distal from the front plug end 202. In this embodiment, the protrusion member has, but is not limited to, two protrusion ribs 203 (only one is shown) that are formed respectively on top and bottom surfaces of the outer housing 201.

The clip 1 is configured to detachably hold the outer housing 201 of the fiber optic connector 200. The clip 1 includes a front engaging portion that is configured to be detachably sleeved on the outer housing 201 of the fiber optic connector 200 and abut against the protrusion member of the outer housing 201, and a rear abutting portion that is configured to abut against the lateral shoulder faces 204 of the outer housing 201.

Figure 5:
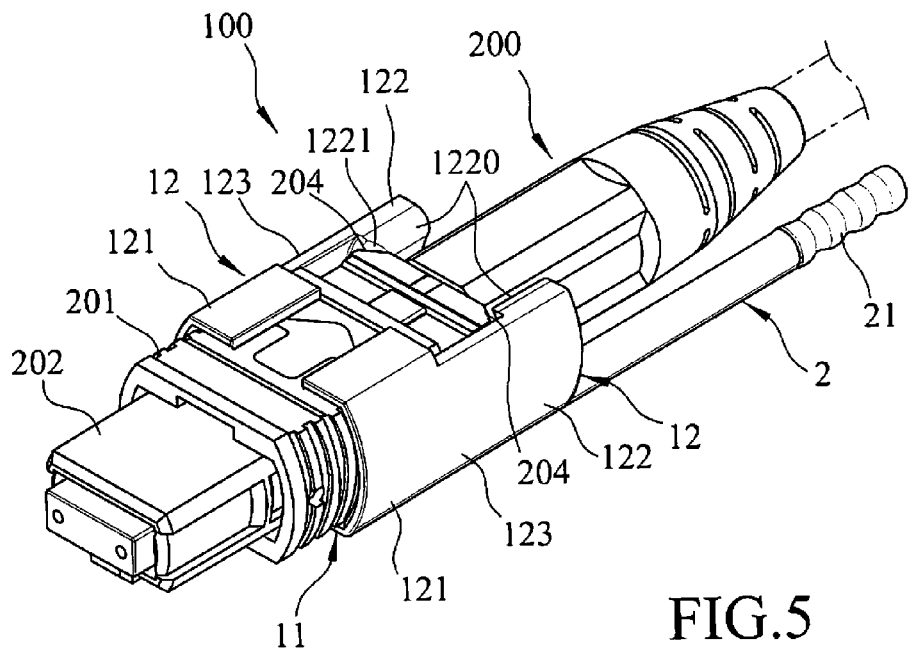
FIG. 5 is a bottom perspective view showing the connector assembly.

In this embodiment, the clip 1 includes a clip base 11 that has an inner surface (i.e., bottom surface) facing the top surface of the outer housing 201, and opposite resilient clip arms 12 that extend respectively from opposite lateral sides of the clip base 11 and that clamp the outer housing 201 therebetween. The clip base 11 is in the form of a plate body, and is formed with a central opening 110 for dividing the clip base 11 into a front base portion 111 and a rear base portion 112. The front base portion 111 of the clip base 11 is configured to abut against the top surface of the outer housing 201 (see FIG. 6). The central opening 110 in the clip base 11 is configured to permit the protrusion rib 203 on the top surface of the outer housing 201 to extend thereinto. Each clip arm 12 has a front arm portion 121 that corresponds to the front base portion 111 of the clip base 11 in position and is configured to abut against a corresponding one of opposite lateral sides of the outer housing 201, a rear arm portion 122 that corresponds to the rear base portion 112 of the clip base 11 in position, and an intermediate arm portion 123 that interconnects the front arm portion 121 and the rear arm portion 122 and corresponds to the central opening 110 in the clip base 11 in position. Therefore, the front base portion 111 of the clip base 11 and the front arm portions 121 of the clip arms 12 cooperatively constitute the front engaging portion of the clip 1. The rear base portion 112 of the clip base 11 and the rear arm portions 122 of the clip arms 12 cooperatively constitute the rear abutting portion of the clip 1. It is noted that the front arm portion 121 of each clip arm 12 has an inwardly bent latch extension 1211 that is configured to abut against the bottom surface of the outer housing 201 (see FIG. 6). In addition, the rear arm portion 122 of each clip arm 12 has an inwardly extending abutting block 1220 that has an inclined front end face 1221, which is configured to abut against a corresponding lateral shoulder face 204 of the outer housing 201, as best shown in FIG. 5.

Furthermore, the clip base 11 and the clip arms 12 may be dimensioned in order to accommodate a different size or a different type of the fiber optic connector 200, such as a subscribe connector or a standard connector (SC).

Figure 3:
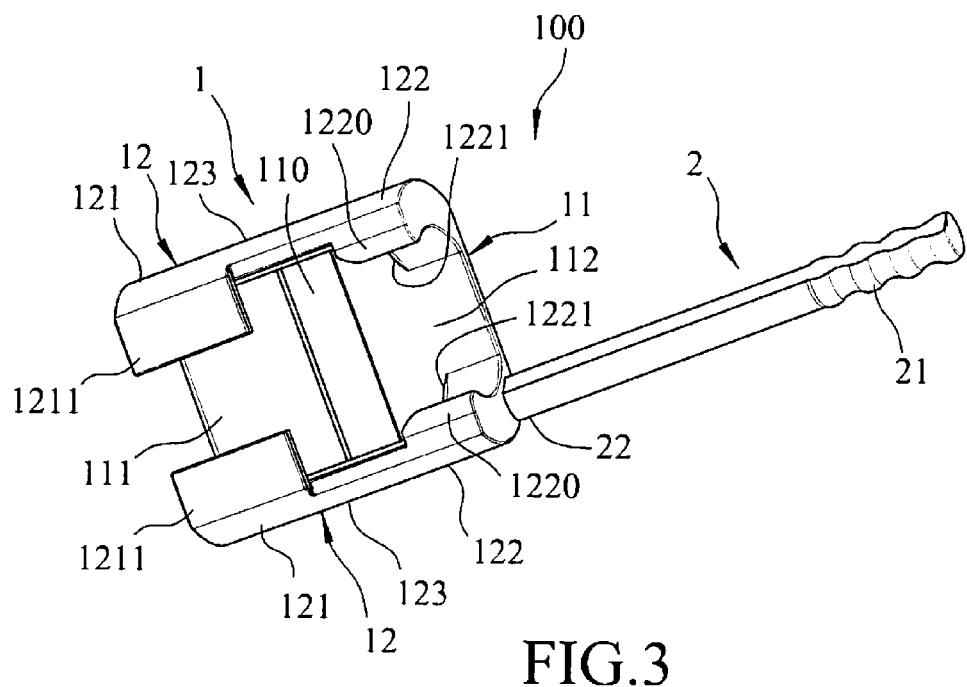
FIG. 3 is a bottom perspective view showing the preferred embodiment.
Figure 4:
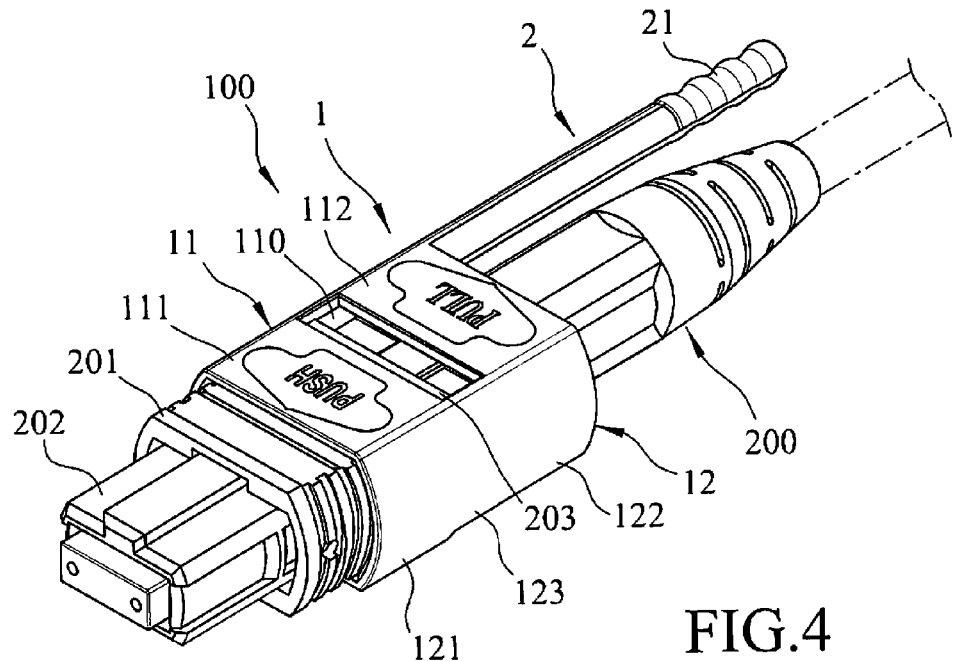
FIG. 4 is a top perspective view showing a connector assembly including the preferred embodiment and the fiber optic connector of FIG. 1.

The gripping handle 2 extends rearwardly from the rear abutting portion of the clip 1. In this embodiment, the gripping handle 2 is in the form of an elongate rod. As shown in FIG. 3, the gripping handle 2 has a connecting end 22 connected integrally to the abutting block 1220 of the rear arm portion 122 of one clip arm 12, and an anti-slip end 21 opposite to the connecting end 22. The anti-slip end 21 has a wavy outer surface for achieving anti-slip effect.

Referring again to FIGS. 4 to 6, when in use, the clip 1 holds the outer housing 201 of the fiber optic connector 200. The front plug end 202 of the fiber optic connector 200 is configured to be inserted into an adaptor (not shown in the drawings).

Figure 6:
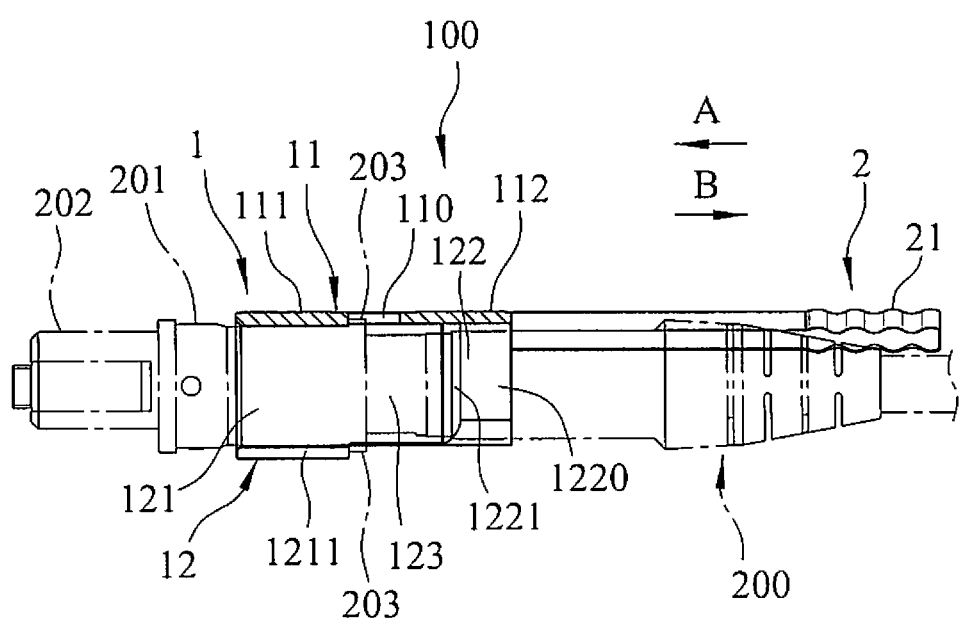
FIG. 6 is a schematic sectional view showing the preferred embodiment.

When it is desired to insert the fiber optic connector 200 into the adaptor, a frontward insertion force indicated by the arrow (A) in FIG. 6 may be applied to the gripping handle 2. In this case, the front end faces 1221 of the abutting blocks 1220 of the rear arm portions 122 of the clip arms 12 abut respectively against the lateral shoulder surfaces 204 of the outer housing 201 (see FIG. 5). Therefore, the frontward insertion force is transmitted from the rear abutting portion of the clip 11 to the lateral shoulder faces 204 of the outer housing 201, thereby facilitating insertion of the fiber optic connector 200 into the adaptor.

When it is desired to remove the fiber optic connector 200 from the adaptor, a rearward removal force indicated by the arrow (B) in FIG. 6 may be applied to the gripping handle 2. In this case, a rear end of the front base portion 111 of the clip base 11 abuts against a front end of said one of the protrusion ribs 203 (i.e., an upper one in FIG. 6) of the outer housing 201 while rear ends of the latch extensions 1211 of the front ram portions 121 of the clip arms 12 abut against the other protrusion rib 203 (i.e., a lower one in FIG. 6). Therefore, the rearward removal force is transmitted from the front engaging portion of the clip 1 to the protrusion ribs 203 of the outer housing 201, thereby facilitating removal of the fiber optic connector 200 from the adaptor.

To sum up, the clip device 100 of the present invention allows the forward insertion force and the rearward removal force applied to the gripping handle 2 to be evenly transmitted to the outer housing 201 of the fiber optic connector 200 without having to grab the fiber optic connector 200 with a user's hand and then push or pull the fiber optic connector 200 into or out from the adaptor. The clip device 100 of the present invention may be particularly useful when the fiber optic connector 200 is used in a high connector density environment. In addition, the clip device 100 of the present invention has a relatively simple structure, and can be easily dimensioned to accommodate a variety of connectors.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. A clip device for facilitating insertion and removal of a push-pull fiber optic connector, the fiber optic connector including an outer housing that permits a front plug end to extend out thereof, the outer housing having a protrusion member proximate to the front plug end, and opposite lateral shoulder faces distal from the front plug end, said clip device comprising:
   a clip adapted to detachably hold the outer housing of the fiber optic connector, said clip including a front engaging portion that is adapted to be detachably sleeved on the outer housing of the fiber optic connector and that is adapted to be disposed in front of and abut against the protrusion member of the outer housing of the fiber optic connector, and a rear abutting portion that is adapted to be disposed behind and abut against the lateral shoulder faces of the outer housing of the fiber optic connector; and
   a gripping handle extending from said rear abutting portion of said clip;
   wherein, when said clip holds the outer housing of the fiber optic connector, a rearward removal force applied to said gripping handle is transmitted from said front engaging portion of said clip to the protrusion member of the outer housing of the fiber optic connector, thereby facilitating removal of the fiber optic connector; and
   wherein, when said clip holds the outer housing of the fiber optic connector, a frontward insertion force applied to said gripping handle is transmitted from said rear abutting portion of said clip to the lateral shoulder faces of the outer housing of the fiber optic connector, thereby facilitating insertion of the fiber optic connector.

2. The clip device as claimed in claim 1, wherein:
   said clip includes a clip base that has an inner surface adapted to face one of top and bottom surfaces of the outer housing of the fiber optic connector, and opposite clip arms that extend respectively from opposite lateral sides of said clip base and that are adapted to clamp the outer housing of the fiber optic connector therebetween, said clip base being formed with a central opening for dividing clip base into a front base portion and a rear base portion, said front base portion being adapted to abut against said one of the top and bottom surfaces of the outer housing of the fiber optic connector, each of said clip arms having a front arm portion that corresponds to said front base portion of said clip base in position and is adapted to abut against a corresponding one of opposite lateral sides of the outer housing of the fiber optic connector, a rear arm portion that corresponds to said rear base portion of said clip base in position, and an intermediate arm portion that interconnects said front arm portion and said rear arm portion and corresponds to said central opening in said clip base in position; and
   said front base portion of said clip base, and said front arm portions of said clip arms cooperatively constitute said front engaging portion of said clip, and said rear base portion of said clip base, and said rear arm portions of said clip arms cooperatively constitute said rear abutting portion of said clip.

3. The clip device as claimed in claim 2, the protrusion member having two protrusion ribs that are formed respectively on the top and bottom surfaces of said outer housing, wherein:
said central opening in said clip base of said clip is adapted to permit one of the protrusion ribs on said one of the top and bottom surfaces of the outer housing to extend thereinto;
said front arm portion of each of said clip arms has an inwardly bent latch extension that is adapted to abut against the other one of the top and bottom surfaces of the outer housing; and
when the rearward removal force is applied to said gripping handle, said front base portion of said clip base abuts against said one of the protrusion ribs while the latch extensions of said front arm portions of said clip arms abut against the other one of the protrusion ribs.

4. The clip device as claimed in claim 2, wherein:
said rear arm portion of each of said clip arms has an inwardly extending abutting block that has a front end face, which is adapted to abut against a corresponding one of the lateral shoulder faces of the outer housing of the fiber optic connector; and
when the frontward insertion force is applied to said gripping handle, said front end faces of said abutting blocks of said rear arm portions of said clip arms abut respectively against the lateral shoulder faces of the outer housing of the fiber optic connector.

5. The clip device as claimed in claim 1, wherein said gripping handle is in the form of an elongate rod, and has an anti-slip end.

6. A connector assembly comprising:
a fiber optic connector including an outer housing that permits a front plug end to extend out thereof, the outer housing having a protrusion member proximate to the front plug end, and opposite lateral shoulder faces distal from the front plug end; and
a clip device including:
a clip detachably holding the outer housing of the fiber optic connector, said clip including a front engaging portion that is detachably sleeved on the outer housing of the fiber optic connector and that is disposed in front of and abuts against the protrusion member of the outer housing of the fiber optic connector, and a rear abutting portion that is disposed behind and abuts against the lateral shoulder faces of the outer housing of the fiber optic connector; and
a gripping handle extending from said rear abutting portion of said clip;
wherein, when said clip holds the outer housing of the fiber optic connector, a rearward removal force applied to said gripping handle is transmitted from said front engaging portion of said clip to the protrusion member of the outer housing of the fiber optic connector, thereby facilitating removal of the fiber optic connector; and
wherein, when said clip holds the outer housing of the fiber optic connector, a frontward insertion force applied to said gripping handle is transmitted from said rear abutting portion of said clip to the lateral shoulder faces of the outer housing of the fiber optic connector, thereby facilitating insertion of the fiber optic connector.

7. The connector assembly as claimed in claim 1, wherein:
said clip includes a clip base that has an inner surface facing one of top and bottom surfaces of the outer housing of the fiber optic connector, and opposite clip arms that extend respectively from opposite lateral sides of said clip base for clamping the outer housing of the fiber optic connector therebetween, said clip base being formed with a central opening for dividing clip base into a front base portion and a rear base portion, said front base portion abutting against said one of the top and bottom surfaces of the outer housing of the fiber optic connector, each of said clip arms having a front arm portion that corresponds to said front base portion of said clip base in position and that abuts against a corresponding one of opposite lateral sides of the outer housing of the fiber optic connector, a rear arm portion that corresponds to said rear base portion of said clip base in position, and an intermediate arm portion that interconnects said front arm portion and said rear arm portion and corresponds to said central opening in said clip base in position; and
said front base portion of said clip base, and said front arm portions of said clip arms cooperatively constitute said front engaging portion of said clip, and said rear base portion of said clip base, and said rear arm portions of said clip arms cooperatively constitute said rear abutting portion of said clip.

8. The connector assembly as claimed in claim 2, wherein:
the protrusion member has two protrusion ribs that are formed respectively on the top and bottom surfaces of said outer housing;
said central opening in said clip base of said clip permits one of the protrusion ribs on said one of the top and bottom surfaces of the outer housing to extend thereinto;
said front arm portion of each of said clip arms has an inwardly bent latch extension that abuts against the other one of the top and bottom surfaces of the outer housing; and
when the rearward removal force is applied to said gripping handle, said front base portion of said clip base abuts against said one of the protrusion ribs while the latch extensions of said front arm portions of said clip arms abut against the other one of the protrusion ribs.

9. The connector assembly as claimed in claim 2, wherein:
said rear arm portion of each of said clip arms has an inwardly extending abutting block that has a front end face, which abuts against a corresponding one of the lateral shoulder faces of the outer housing of the fiber optic connector; and
when the frontward insertion force is applied to said gripping handle, said front end faces of said abutting blocks of said rear arm portions of said clip arms abut respectively against the lateral shoulder faces of the outer housing of the fiber optic connector.

10. The connector assembly as claimed in claim 1, wherein said gripping handle is in the form of an elongate rod, and has an anti-slip end.

* * * * *